(12) United States Patent
Ho et al.

(10) Patent No.: US 7,229,440 B2
(45) Date of Patent: Jun. 12, 2007

(54) BENDABLE CUTTING DEVICE

(75) Inventors: Huddee Jacob Ho, San Jose, CA (US); Roberta Lee, Redwood City, CA (US); Samuel E. Zuckswert, San Jose, CA (US); Stanley R. Conston, San Carlos, CA (US); Ronald Yamamoto, San Francisco, CA (US); Don Alden, Sunnyvale, CA (US)

(73) Assignee: Manoa Medical, Inc., Redwood City, CA (US)

( * ) Notice: Subject to any disclaimer, the term of this patent is extended or adjusted under 35 U.S.C. 154(b) by 106 days.

(21) Appl. No.: 10/783,714

(22) Filed: Feb. 20, 2004

(65) Prior Publication Data

US 2004/0220564 A1 Nov. 4, 2004

Related U.S. Application Data

(60) Provisional application No. 60/449,061, filed on Feb. 20, 2003.

(51) Int. Cl.
*A61B 18/14* (2006.01)
(52) U.S. Cl. .......................... 606/47; 606/113; 606/114
(58) Field of Classification Search ................. 606/47, 606/113–114
See application file for complete search history.

(56) References Cited

U.S. PATENT DOCUMENTS

| | | | | | |
|---|---|---|---|---|---|
| 3,739,784 | A | * | 6/1973 | Itoh | 606/113 |
| 4,503,855 | A | * | 3/1985 | Maslanka | 606/47 |
| 5,078,716 | A | * | 1/1992 | Doll | 606/47 |
| 5,171,233 | A | * | 12/1992 | Amplatz et al. | 604/540 |
| 5,190,542 | A | * | 3/1993 | Nakao et al. | 606/47 |
| 5,190,555 | A | * | 3/1993 | Wetter et al. | 606/114 |
| 5,192,286 | A | * | 3/1993 | Phan et al. | 606/127 |
| 5,201,741 | A | * | 4/1993 | Dulebohn | 606/113 |
| 5,336,227 | A | * | 8/1994 | Nakao et al. | 606/114 |
| 5,415,656 | A | * | 5/1995 | Tihon et al. | 606/46 |
| 6,068,603 | A | * | 5/2000 | Suzuki | 600/565 |
| 6,123,665 | A | * | 9/2000 | Kawano | 600/104 |
| 6,331,166 | B1 | * | 12/2001 | Burbank et al. | 600/567 |
| 6,500,113 | B2 | | 12/2002 | Vilos | |
| 6,852,111 | B1 | * | 2/2005 | Lieber | 606/47 |
| 2002/0072688 | A1 | | 6/2002 | Burbank et al. | |
| 2003/0109874 | A1 | * | 6/2003 | Dennis | 606/47 |
| 2003/0163129 | A1 | * | 8/2003 | Lee et al. | 606/47 |

FOREIGN PATENT DOCUMENTS

WO    WO 02/100286    12/2002

* cited by examiner

*Primary Examiner*—Michael Peffley
*Assistant Examiner*—Alex Toy
(74) *Attorney, Agent, or Firm*—Jung-hua Kuo (57) ABSTRACT

Devices and methods for a minimally invasive procedure for cutting tissue are disclosed. The device generally includes a probe with a distal exit at an exit angle relative to the probe, a cutting loop with shape memory having a preconfigured shape, and a loop securing mechanism to secure the cutting loop in a penetrating configuration and to release the cutting loop into a cutting configuration. The cutting loop is generally within a profile of the probe in the penetrating configuration. In the cutting configuration, the cutting loop extends through the cutting loop exit and generally returns to the preconfigured shape at a cutting angle generally defined by the exit angle. The cutting loop securing mechanism may be, for example, a cover slidable over the probe, a slidable member extending from a distal tip of the probe, or a groove defined in the probe proximal to the cutting loop exit.

32 Claims, 6 Drawing Sheets

BENDABLE CUTTING DEVICE

CROSS REFERENCE TO RELATED APPLICATIONS

This application claims priority to U.S. Provisional Patent Application Ser. No. 60/449,061 filed on Feb. 20, 2003 which is incorporated herein by reference in its entirety.

BACKGROUND OF THE INVENTION

1. Field of the Invention

The present invention relates generally to devices and methods for cutting soft tissue. More specifically, devices and methods for a minimally invasive procedure for cutting or excising a volume of soft tissue such as a biopsy or a therapeutic excision of cancer are disclosed.

2. Description of Related Art

Minimally invasive procedures have instigated a need for refinement in surgical devices that can function within confined spaces, particularly in soft tissue, such as breast tissue. Devices that are typically used during open surgical procedures (i.e., scalpel, scissors, electrosurgical "pencil" electrode) are often not adaptable for use in a minimally invasive procedure. In addition, the actual procedure cannot be directly visualized as the skin incision is typically just large enough to insert the device. Minimally invasive procedures are often guided by medical imaging or by video camera as is often used in laparoscopy. In the breast, mammography, ultrasound and magnetic resonance imaging (MRI) are used to guide minimally invasive procedures. Current devices that use an oscillating sharp edge or radio frequency energy to cut the tissue retrieve a specimen of fixed volume and are not adaptable to excise lesions of different sizes or include extensions of the lesion or disease process in the excision. In particular, breast cancer often extends towards the nipple within a milk duct or towards the skin in Cooper's ligament in addition to growing outward in a radial direction. Current minimally invasive devices are designed to excise a mass and are not adaptable for excision of an associated diseased duct or Cooper's ligament. Leaving cancer behind in the duct or in Cooper's ligament increases the risk of local recurrence despite the administration of post operative radiation therapy.

Open surgical biopsy removes lesions of variable size and may include extensions of the lesion but often an excessive amount of normal breast tissue is included in the specimen leading to a poor cosmetic result. In addition, open surgical biopsy typically requires a significant skin incision resulting in a longer, permanent scar. More importantly, a diseased duct and/or disease in Cooper's ligament are not detectable either by direct vision or by palpation during an open surgical procedure. The main cancerous mass may be excised, but a diseased duct filled with cancerous cells and/or diseased Cooper's ligament is often not appreciated during the procedure and unintentionally not included in the excision.

Axial ductal ultrasound is a method of ultrasound scanning of the breast that demonstrates the internal anatomy of the breast. In particular, the ducts and lobes of the breast are identified resulting in visualization of not only a lesion, but also diseased duct(s) and extension into Cooper's ligament. Multifocal cancers or additional cancers associated with the diseased duct may also be visualized. Therefore, the entire disease process (i.e., the lesion and extensions of the lesion within the breast) is visualized and can be removed under direct, real-time ultrasound guidance.

Accordingly, there is a need for a device and method for a minimally invasive procedure that excises lesions of variable size within a volume of tissue from a breast or other soft tissue. More specifically, there is a need for a device and method to excise a disease process within a breast that includes not only the main focus of the disease (i.e., a lesion or a mass) but also the duct or ducts that are also affected and any other anatomic extension of the disease process (e.g., growth into Cooper's ligament). Preferably the procedure is guided using medical imaging.

SUMMARY OF THE INVENTION

Devices and methods for a minimally invasive procedure for cutting or excising a volume of soft tissue such as a biopsy or a therapeutic excision of cancer are disclosed. It should be appreciated that the present invention can be implemented in numerous ways, including as a process, an apparatus, a system, a device, or a method. Several inventive embodiments of the present invention are described below.

The device for excising a volume of soft tissue generally includes a probe containing a cutting loop. The probe has a length defining a probe axis while the cutting loop has a loop height defining a loop axis. The loop is preferably made from a metal or metal alloy having superelastic properties or shape memory capability such that the angle between the loop axis relative to the probe axis can be configured to one or more positions. When the probe is penetrating into soft tissue during positioning, the loop is in a penetrating configuration where the loop axis is configured to align at an angle that is generally approximately 180 degrees relative to the probe axis to facilitate ease of penetration. After the probe is positioned in the desired location, the loop preferably moves to a cutting configuration such that the angle between the loop axis and the probe axis is generally approximately 90 degrees. The loop exits the probe through angled exits which determine the angle of the loop axis relative to the probe axis when the loop is in the cutting configuration. To assume the penetrating configuration, the loop may be manually or mechanically forced into the penetrating configuration and held in place. When released, the loop moves to the cutting configuration. The change in angle of the loop axis relative to the probe axis is facilitated by the superelastic property or the shape memory capability of the metal or metal alloy used to configure the loop. The superelastic property allows the loop to change configuration without developing a kink or permanent deformity in the loop. To facilitate cutting of soft tissue, the loop may have one or more sharpened edges. In addition, the loop may be energized such as with radio frequency energy and/or the loop may be configured to oscillate along a predetermined or variable distance, direction and/or frequency. The loop shape and/or sized may be fixed or variable by adjusting the width and/or height of the loop.

A method for cutting a volume of soft tissue generally includes scanning the soft tissue with an imaging device and determining the volume of soft tissue to be excised. Preferably the volume of soft tissue contains at least one of a lesion, a duct or ducts, a Cooper's ligament and a lobe or part of a lobe. Preferably, the probe is positioned in the soft tissue adjacent to the targeted volume of soft tissue with the loop in the penetrating configuration. Energy such as radio frequency energy may be used to facilitate tissue penetration. Once the probe is positioned in the desired location the loop is released from the penetrating configuration and moved to the cutting configuration. After the loop is in the cutting configuration, the probe is advanced or retracted to move the loop creating a circumferential cut around the volume of soft tissue. The loop may be expanded and/or retracted in width and/or height to accommodate variations in the desired volume of soft tissue being excised. During the positioning of the probe and/or the cut, the loop may be energized from an external energy source (e.g., radio frequency energy) and/or may oscillate. Oscillation of the loop is typically independent of the probe advancement or retraction and may be in one of several directions. Once on the opposite side of the volume soft tissue from where the cut was initiated, the loop is retracted into the probe or, in an alternative, the loop is mechanically forced into the penetrating configuration to complete the cutting process. The procedure may be guided using an imaging device. The imaging device may be external to the patient or the imaging device may be incorporated into the probe.

These and other features and advantages of the present invention will be presented in more detail in the following detailed description and the accompanying figures which illustrate by way of example principles of the invention.

BRIEF DESCRIPTION OF THE DRAWINGS

The present invention will be readily understood by the following detailed description in conjunction with the accompanying drawings, wherein like reference numerals designate like structural elements.

DESCRIPTION OF SPECIFIC EMBODIMENTS

Devices and methods for a minimally invasive procedure for cutting or excising a volume of soft tissue such as a biopsy or a therapeutic excision of cancer are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that is known in the technical fields related to the invention have not been described in detail so as not to unnecessarily obscure the present invention.

Figure 1A:
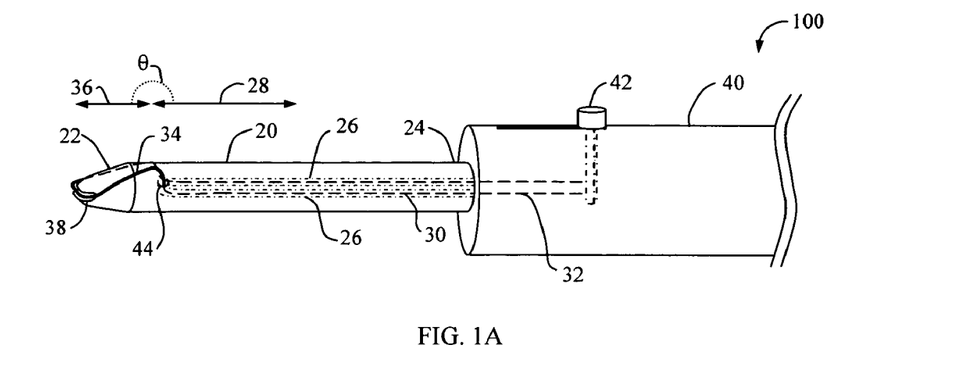
FIGS. 1A and 1B are perspective side views of an exemplary embodiment of a cutting device with a bendable loop in a penetrating and a cutting configuration, respectively.
Figure 1B:
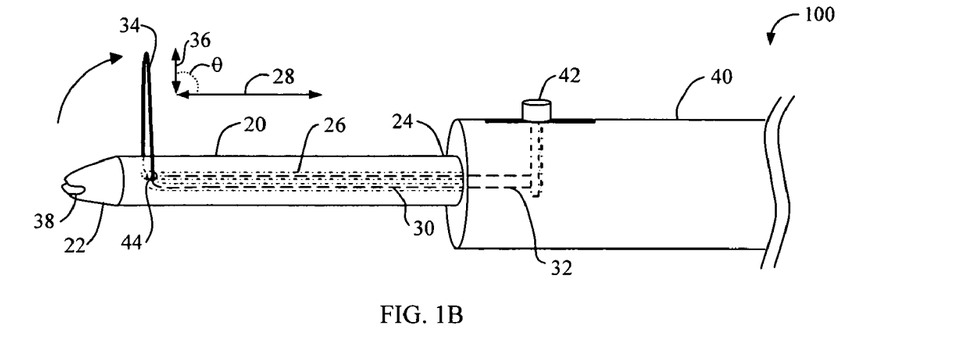

FIGS. 1A and 1B are perspective views of an exemplary embodiment of a cutting device 100 with a bendable loop 34 in a retracted and an extended position, respectively. As shown in FIG. 1A, the cutting device 100 generally comprises a probe 20 and a handle 40. The probe 20 defines a probe axis 28 between a proximal end 24 and a distal end 22. Loop channels 26, contained within the probe 20 and generally aligned along the probe axis 28, terminate at angled exits 44 located at or near the distal end 22. Prior to terminating at the angled exits 44, the loop channels 26 change alignment from being one of generally aligned with the probe axis 28, to being one of at an angle relative to the probe axis 28. The loop channels 26 may contain an electrode 30. The electrode 30 terminates in electrode ends 32 in the proximal end 24 or the handle 40, as shown in FIG. 1A. The electrode 30 extends out of the cutting device 100 at the angled exits 44 such that the electrode 30 between the angled exits 44 creates the bendable loop 34.

Figure 1C:
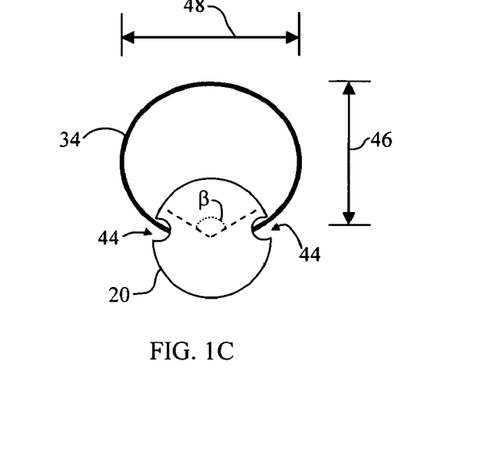
FIGS. 1C and 1D are cross-sectional views of alternative embodiments of the cutting device.
Figure 1D:
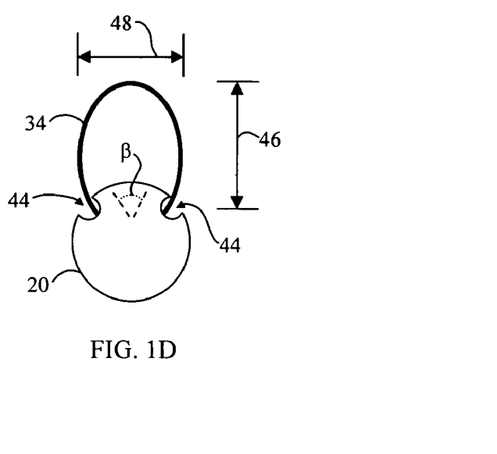
Figure 1E:
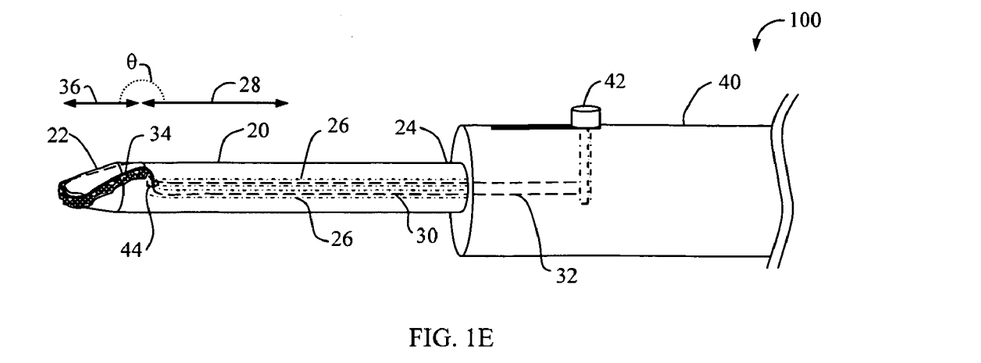
FIGS. 1E and 1F illustrate the cutting device of FIG. 1A with a tissue collector in a penetrating and a cutting configuration, respectively.
Figure 1F:
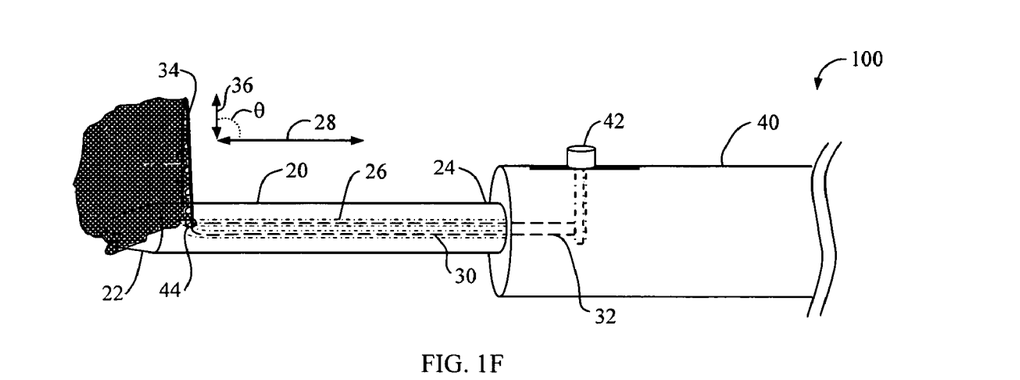

In cross-sectional views of alternative embodiments illustrated in FIGS. 1C and 1D, extension of the loop 34 out of the angled exits 44 defines a loop height 46. A loop width 48 is determined by an angle β between the angled exits 44. Preferably the angle β is predetermined although the angle β may be variable. As shown in FIG. 1C the angle β defines a loop width 48 that is larger than the loop width 48 in the alternative embodiment illustrated in FIG. 1D. In yet another alternative (not shown) at least one of the loop channels 26 is a rotatable tube that terminates at the angled exit 44. Rotating one or more rotatable tubes varies the angle β which varies the loop width 48.

The probe 20 and handle 40 may be configured from any number of materials including metals, metal alloys, ceramics and/or plastics. The probe 20 and handle 40 may be configured as a single unit or as one or more separate units that are fastened together. Preferably the electrode 30 is made from a nickel titanium alloy (nitinol) with shape memory or superelastic property although any other suitable metal or metal alloy with shape memory or superelastic properties may be employed.

Figure 4A:
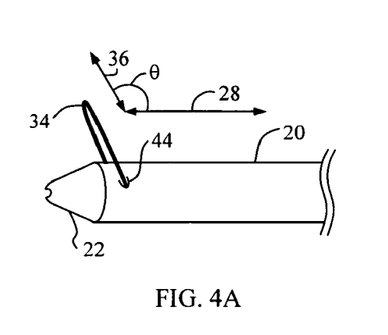
FIGS. 4A and 4B are perspective views illustrating exemplary configurations of the loop in the cutting configuration.
Figure 4B:
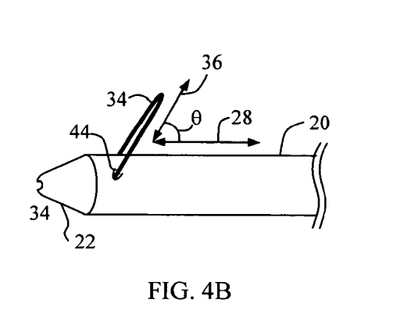

FIG. 1B illustrates the loop 34 in a cutting configuration. At least one of the angled exits 44 and/or the shape memory properties of the electrode 30 (e.g., nitinol) facilitate in configuring the loop 34 to the cutting configuration. The angled exits 44 determine a loop axis 36 defined by the loop 34 relative to the probe axis 28. A loop angle θ is defined between the probe axis 28 and the loop axis 36. The loop 34 assumes the cutting configuration when the loop 34 is at least partially extended through the angled exits 44. Preferably, the angled exits 44 configure the loop 34 such that the loop angle θ is generally 90 degrees although the loop angle θ may be less than or greater than 90 degrees as in the embodiments illustrated in FIGS. 4A and 4B, for example. In one exemplary embodiment, the angled exits 44 may be configured such that the loop angle θ is greater than 90 degrees, as illustrated in FIG. 4A. In an alternative embodiment, the angled exits 44 may be configured such that the loop angle θ is less than 90 degrees, as illustrated in FIG. 4B.

In an alternative (not shown), the loop 34 is preformed to a predetermined cutting configuration preferably before the electrode 30 is assembled into the cutting device 100. The process of preforming a loop to the predetermined configuration is well known to those skilled in the art. In particular, the electrode 30 can be positioned and maintained such that the loop 34 is in the predetermined cutting configuration and heated to a specified temperature for a predetermined length of time followed by rapid cooling. The temperature and length of time may be varied according to the type of material used for the electrode 30. Preferably the loop 34 is preformed such that the loop angle θ is approximately 90 degrees.

Referring back to FIG. 1A, the loop 34 is shown in a penetrating configuration where the loop 34 is positioned such that the loop angle θ is approximately 180 degrees. A groove 38 located at or near the distal end 22 of the probe 20 holds the loop 34 in the penetrating configuration. The loop 34, which is in the cutting configuration when at least partially extended (as shown in FIG. 1B), may be manually or mechanically positioned into the penetrating configuration. Preferably the electrode 30 is made of a material having superelastic properties (e.g., nitinol) to allow the loop 34 to be positioned into the penetrating configuration without creating a permanent kink or distortion in the electrode 30. The penetrating configuration is maintained by placement of the loop 34 into the groove 38, followed by slight retraction of the loop 34. The slight retraction keeps the loop 34 tightly held within the groove 38. In an alternative (not shown), a loop locking mechanism may be provided on the handle 40 to secure the loop 34 in the penetrating configuration. A loop controller 42 located on the handle 40 controls extension and retraction of the loop 34. Maintaining the loop 34 in the penetrating configuration enhances insertion of the probe 20 into soft tissue by creating a more linear profile to the probe 20. Keeping the partially extended loop 34 external to the probe 20 and held within the groove 38 allows for a smaller diameter probe 20. In an alternative (not shown), the loop 34 may be manually or mechanically positioned by the methods described herein such that the loop 34 is angled proximal to the angled exits 44 to assume an alternative penetrating configuration.

Figure 3A:
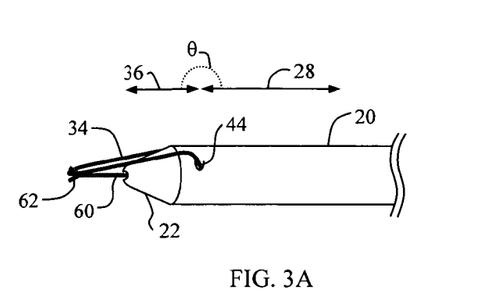
FIGS. 3A–3F are perspective views of further alternative exemplary embodiments of the cutting device with a bendable loop.
Figure 3B:
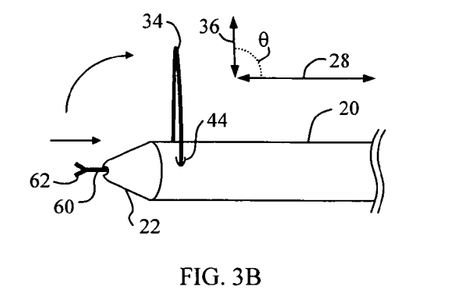
Figure 3C:
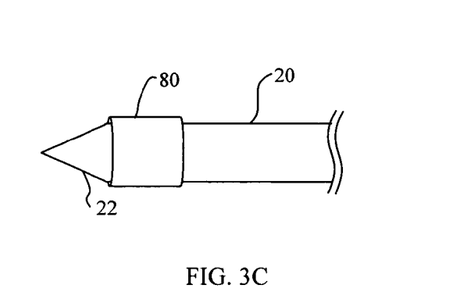
Figure 3D:
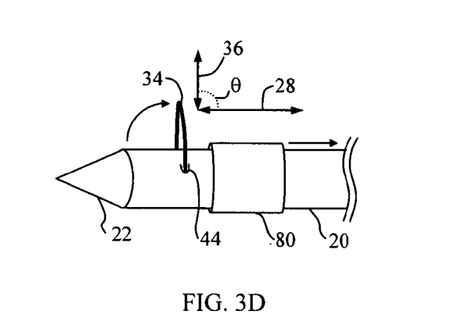
Figure 3E:
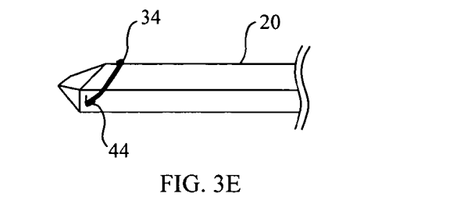
Figure 3F:
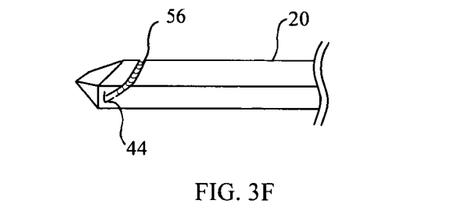

In an alternative embodiment illustrated in FIG. 3E, the loop 34 is further retracted into the probe 20 such that only a minimum length of the loop 34 is outside of the probe 20 as determined by the distance between the angled exits 44. Preferably the distance between the angled exits 44 is of sufficient length to prevent a kink or permanent deformity in the loop 34 when the loop 34 is retracted. In a further alternative illustrated in FIG. 3F, the probe 20 defines a groove 56 near the angled exits 44. The loop 34 (not shown) is positioned in the groove 56 when the loop 34 is retracted. In yet further alternatives (not shown), the retracted loop 34 may be positioned in a partial groove or in an opening in the probe.

Referring back to FIG. 1B, the loop 34 is further extended by the loop controller 42 and is in a cutting configuration. Further extension of the loop 34 increases the size of and releases the loop 34 from the groove 38 which allows the loop 34 to move to the cutting configuration. The change in the loop angle θ when the loop 34 moves from the penetrating configuration to the cutting configuration is preferably facilitated by the superelastic properties of the metal or metal alloy of the electrode 30. In the exemplary embodiment, the loop angle θ is approximately 90 degrees when the loop 34 is in the cutting configuration. Cutting around a volume of soft tissue is accomplished by advancing and/or retracting the probe 20 when the loop 34 is in the cutting configuration. Extension and/or retraction of the loop 34 are preferably controlled by movement of one and/or both of the electrode ends 32.

To facilitate positioning of the probe 20 in the tissue, the probe 20 and/or the loop 34 may contain a locating mechanism (not shown) to aid in determining the location of the probe 20 and/or the loop 34 within the tissue. A detecting mechanism, preferably located external to the tissue, detects the locating mechanism. The locating mechanism may include radiologic or ultrasound markers, light or other signal emitters, or such other mechanism as may be detectable by the corresponding detecting mechanism typically external to the patient.

The cross-sectional area of the electrode 30 may be round, square, triangular, rectangular, oval, diamond-shaped, polygonal or any other desired shape. One or more cutting edges on the loop 34 and/or electrode 30 may be sharpened or serrated. The electrode 30 may be in continuity with an external energy source (not shown) such as but not limited to radio frequency energy, laser and/or vibration. Other methods of cutting soft tissue may be incorporated into the loop and/or electrode including but not limited to air abrasion and/or water jet. Where the electrode 30 is energized with radio frequency, an electrical circuit may be configured as a monopolar system with the loop acting as the active electrode and a larger, dispersive grounding pad acting as the return electrode. In an alternative, the return electrode may be positioned on or near the cutting device 100 resulting in a bipolar system. Furthermore, the loop 34 and/or electrode 30 may be partially or completely insulated to expose the radio frequency energy to the tissue at one or more predetermined locations on the loop 34. Materials that may act as insulators include but are not limited to ceramics and polymers such as polymethylsiloxane, paratetrafluoroethylene, polyimide, and/or polyetheretherketone. The loop 34 may oscillate along one or more predetermined directions to facilitate the cutting of soft tissue. The loop 34 may oscillate by movement of the electrode 30 within the loop channels 26. In an alternative, the loop 34 may oscillate by movement of the probe 20.

Figure 2A:
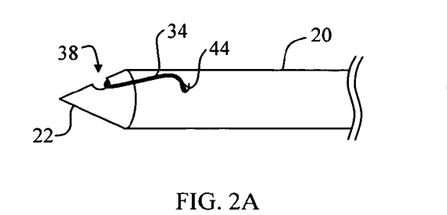
FIGS. 2A and 2B are perspective views of alternative exemplary embodiments of the cutting device with a bendable loop.
Figure 2B:
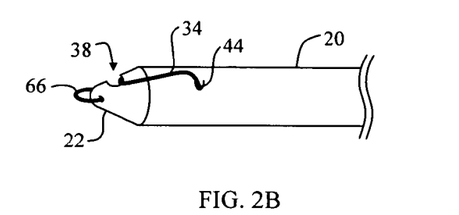

To facilitate tissue penetration, the loop 34 may be energized during positioning of the probe 20 when the loop 34 is in the penetrating configuration. In an alternative, as illustrated in FIG. 2A, the groove 38 is proximal to the distal end 22. The distal end 22 is configured as a sharpened tip that may facilitate tissue penetration but the distal end 22 may be any number of configurations that preferably aid in tissue penetration such as a sharpened edge or edges. The distal end 22 may also be energized, for example, with radio frequency energy and/or any other suitable energy. In a further alternative the distal end 22 may contain one or more penetrators 66 that protrude distally as illustrated in the embodiment in FIG. 2B. The penetrator 66 may be sharpened and/or may be energized with, for example, radio frequency energy to facilitate tissue penetration. Preferably energizing of the distal end 22 or the penetrator 66 is independent from and electrically isolated from energizing of the electrode 30. In an alternative (not shown), the penetrator 66 is partially or completely insulated to expose the radio frequency energy to the tissue at one or more predetermined locations on the penetrator 66. Furthermore, the penetrator 66 may oscillate in one or more predetermined directions to facilitate penetration of the soft tissue.

In the embodiment illustrated in FIGS. 3A and 3B, a loop holder 60 is used to maintain the loop 34 in the penetrating configuration. In the exemplary embodiment, a holder end 62 of the loop holder 60 comprises a "Y" shaped configuration but any suitable configuration of the holder end 62 to facilitate maintaining the loop 34 in the penetrating configuration may be used. The loop holder 60 may be retracted by a loop holder controller located on the handle (not shown), for example, such that the loop 34 is released from the holder end 62 and moves to the cutting configuration.

In an alternative embodiment illustrated in FIGS. 3C and 3D, a loop cover 80 is configured at least partially around the probe 20 and moves along the probe axis 28. As illustrated in FIG. 3C, the loop cover 80 is at or near the distal end 22 and positions the loop 34 in the penetrating configuration. When the loop cover 80 is moved along the probe axis 28 proximally toward the handle, the loop 34 is uncovered and no longer restricted by the loop cover 80 and moves to the cutting configuration as shown in FIG. 3D. The loop cover 80 is preferably controlled by a loop cover controller (not shown) located on the handle, for example. The cutting process is completed by retracting the loop 34 into the probe 20 and/or moving the loop cover 80 over the loop 34 to mechanically position the loop 34 into the penetrating configuration. In an alternative (not shown), the loop cover 80 is moved along the probe axis 28 distally away from the handle to uncover the loop 34.

Figure 5:
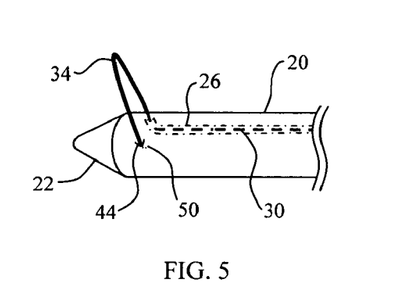
FIG. 5 is a perspective view of yet another alternative exemplary embodiment of the cutting device with a bendable loop.

In the embodiment illustrated in FIG. 5, a fixed end 50 of the electrode 30 is located at or near the distal end 22 of the probe 20 and an electrode end (not shown) of the electrode 30 is located in the proximal end 24 of the probe 20 or in the handle (not shown). The probe 20 contains a single loop channel 26 such that the probe 20 has a smaller profile (e.g., diameter) than where the probe contains multiple loop channels and/or provides more room within the probe 20 for the change in alignment of the loop channel 26 from being generally parallel to the probe axis 28 to terminating at the angled exit 44. The increased room provides for a less acute change of direction, thereby facilitating movement of the electrode 30 within the loop channel 26.

Figure 6:
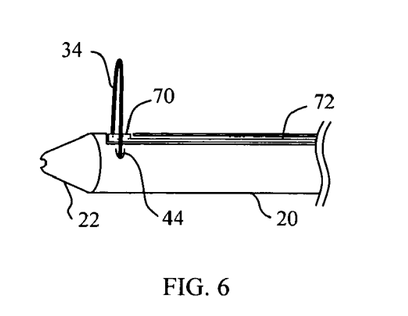
FIG. 6 is a perspective view illustrating an exemplary configuration of an imaging device incorporated into the probe.

In the embodiment illustrated in FIG. 6, an imaging catheter 70 is positioned within the probe 20 such that the imaging catheter 70 scans an imaging area adjacent to or containing the loop 34. The exemplary embodiment shows the imaging catheter 70 in position to image an area containing the loop 34, but the imaging catheter 70 may be positioned in any suitable position along the probe 20. The imaging catheter 70 may be configured to rotate about the probe axis 28 to broaden the imaging area. The imaging catheter 70 is preferably an ultrasound transducer but may also be any other type of suitable imaging modality. The ultrasound transducer preferably has a high frequency in a range between approximately 10 MHz to 100 MHz. The proximity of the ultrasound transducer to the imaged area provides for use of a higher frequency which gives improved resolution of the imaged area. The imaging catheter 70 may acquire images that are processed to show at least a two-dimensional, a three-dimensional and/or a four-dimensional image.

The imaging catheter 70 may be employed during positioning of the probe 20 and/or during the cutting process (i.e., as the probe 20 is advanced or retracted with the loop 34 in the cutting configuration). Preferably the imaging catheter 70 images in real time the loop 34 and the volume of soft tissue being excised during the cutting process. Preferably the imaging catheter 70 and the loop 34 are moved in unison as the probe 20 is advanced or retracted during the cutting process. The imaging catheter 70 may be fixed within the probe 20 or preferably the imaging catheter 70 is configured as a separate component that slides into an imaging channel 72 contained in the probe 20. When advanced to the desired position in the imaging channel 72, the imaging catheter 70 is preferably secured in place with a lock mechanism (not shown). The position of the imaging catheter 70 relative to the loop 34 may be predetermined or varied depending on the positioning of the imaging catheter 70 within the imaging channel 72. The probe 20 and/or the loop 34 may additionally include an enhanced visualization mechanism using medical imaging such as radiologic or ultrasound markers or may include a signaling device to provide emitted signals to be detected by an external detector.

Figure 7A:
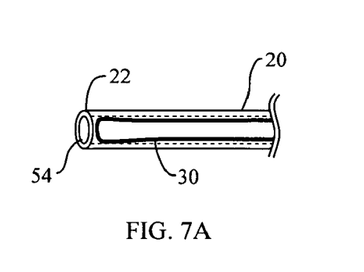
FIGS. 7A and 7B are perspective views of an alternative exemplary embodiment of the cutting device with a bendable loop.
Figure 7B:
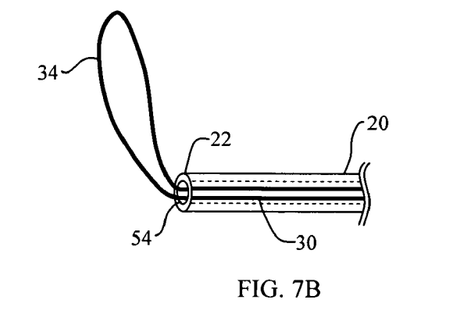

FIGS. 7A and 7B illustrate another embodiment of the cutting device. In FIG. 7A, the electrode 30 is completely contained within the probe 20 in the penetrating configuration. In FIG. 7B, the electrode 30 is shown extending out of the probe 20 in the cutting configuration. The electrode 30 is advanced out of the probe 20 through the exit 54, located at or near the distal end 22, by an advancement controller located on the handle (not shown), for example. When advanced through the exit 54, the shape memory properties of the electrode 30 cause the loop 34 to assume a predetermined size and shape. Configuring the loop 34 to the predetermined size and shape is performed before the electrode is assembled into the cutting device and is well know to those skilled in the art. The superelastic properties of the material allow the loop 34 to be entirely or almost entirely positioned within the probe 20 without creating a kink or permanent deformity in the loop 34. When the loop 34 is advanced out of the probe 20, the loop 34 returns to the predetermined size and shape due to the shape memory properties. The loop 34 may be energized with radio frequency energy, laser and/or vibration, for example, prior to and during advancement through the exit 54. The loop may be partially or completely insulated to facilitate the cutting process. Oscillation of the loop may additionally or alternatively be applied to facilitate the cutting process.

FIGS. 8A–8D are schematics illustrating a cutting process using the cutting device 100 in an area of a breast 90. In the exemplary embodiment, the area of the breast 90 contains a nipple/areolar complex 99 and a lobe 97 containing a duct 96. The duct 96 contains a lesion 94 and a disease extension 95 within the duct 96. An imaging device 110 is preferably used to locate the duct 96, the lesion 94, and disease extension 95 and guide the cutting process. In this exemplary schematic, the imaging device 110 is an ultrasound transducer although any other suitable imaging modality may be used. The imaging device 110 may acquire images that are processed to give two-dimensional, three-dimensional and/or four-dimensional images. In an alternative (not shown), the imaging catheter contained within the probe 20 as described above may be used alone or in conjunction with the imaging device 110 to guide the cutting process.

Figure 8A:
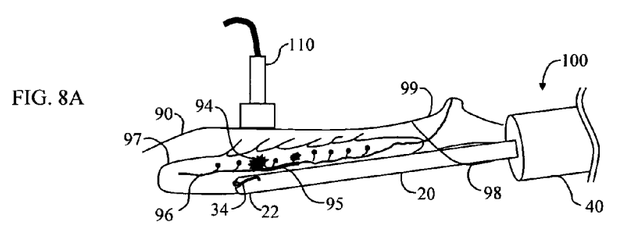
FIGS. 8A–8D are schematics illustrating the cutting device used in conjunction with an imaging device to cut a volume of soft tissue.
Figure 8B:
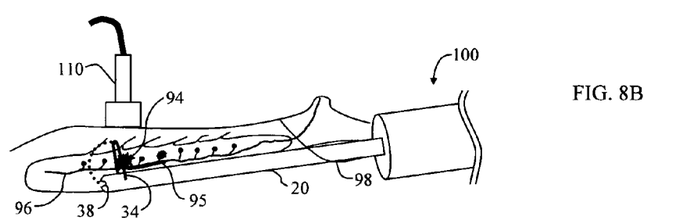
Figure 8C:
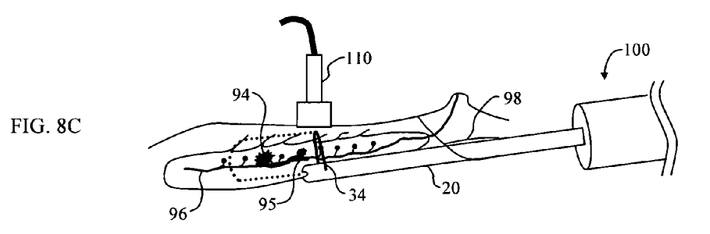
Figure 8D:
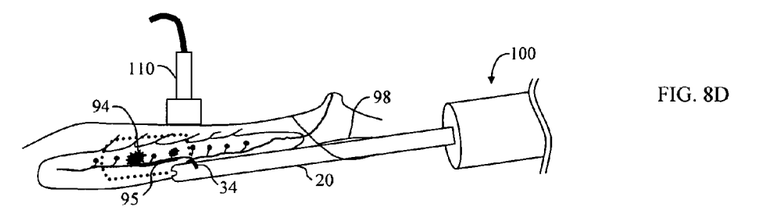

As shown in FIG. 8A, the probe 20 enters the breast 90 through a skin incision 98 that is preferably located at a border of the nipple/areola complex 99. In the exemplary schematic, the probe 20 is positioned under the duct 96 and the lesion 94 but in various alternatives the probe 20 may be positioned on a side of or superficial to the duct 96 and/or lesion 94. Preferably, the distal end 22 is positioned distal to the lesion 94 and any additional disease within the duct 96 (i.e., the disease extension 95) relative to the skin incision 98. The probe 20 is preferably positioned with the loop 34 in the penetrating configuration. The loop 34 may be energized using, for example, an external radio frequency energy source (not shown) to facilitate tissue penetration and positioning of the probe 20. In FIG. 8B, the loop 34 is energized and expanded into the cutting configuration. Expansion releases the loop 34 from the groove 38 and energizing allows the loop 34 to cut through soft tissue as the loop 34 moves into the cutting configuration. The height and width of the loop 34 may be adjusted or varied to ensure that the entire lesion 94 and disease extension 95 is encircled by the loop 34 during the cutting process. Next, the probe 20 is retracted as illustrated in FIG. 8C, causing the loop 34 to cut tissue circumferentially around the lesion 94 and the disease extension 95. The imaging device 110 generally continues to keep the loop 34 and/or the area of tissue adjacent to the loop 34 within the imaging area. For example, if the imaging device 110 is an ultrasound transducer, the ultrasound transducer moves preferably in unison with the loop 34 to keep the loop 34 within the imaging area. In FIG. 8D, the loop 34 is proximal to the lesion 94 and the disease extension 95. The loop 34 is retracted completing the cutting process. Once retracted, energizing of the loop 34 can be terminated. In an alternative (not shown), the distal end of the probe 20 is positioned proximal to the lesion 94 and disease extension 95, the loop 34 is expanded and the probe 20 is advanced to accomplish the cutting process.

During the cutting process, the loop 34 and/or probe 20 may be configured to oscillate or move back and forth in an independent motion that is separate from the advancement or retraction of the probe 20. The independent motion enhances the cutting process. Preferably the independent motion is along a direction defined by the curvature of the loop 34. Alternatively, the independent motion is along any direction or combination of directions defined by the loop axis, the probe axis and/or a direction that is at one or more angles to the loop axis and the probe axis.

In a further alternative embodiment (not shown), a tissue collector is attached to the loop and/or the probe. The tissue collector preferably encompasses the severed tissue during the cutting process or after the cutting process is complete. The tissue collector facilitates in removal of the cut tissue from the breast. In yet a further alternative (not shown), a tissue marking mechanism may be incorporated into the cutting device to facilitate orientation of the cut tissue after removal from the breast. The tissue marking mechanism marks the specimen during the cutting process and/or after the cutting process is complete. In yet another further alternative, a soft tissue orientation and imaging guide system may be incorporated to facilitate targeting of the area of soft tissue to be excised, orient and fixate the area of soft tissue during the cutting process and facilitate movement of the imaging scanner relative to the cutting device.

Figure 9:
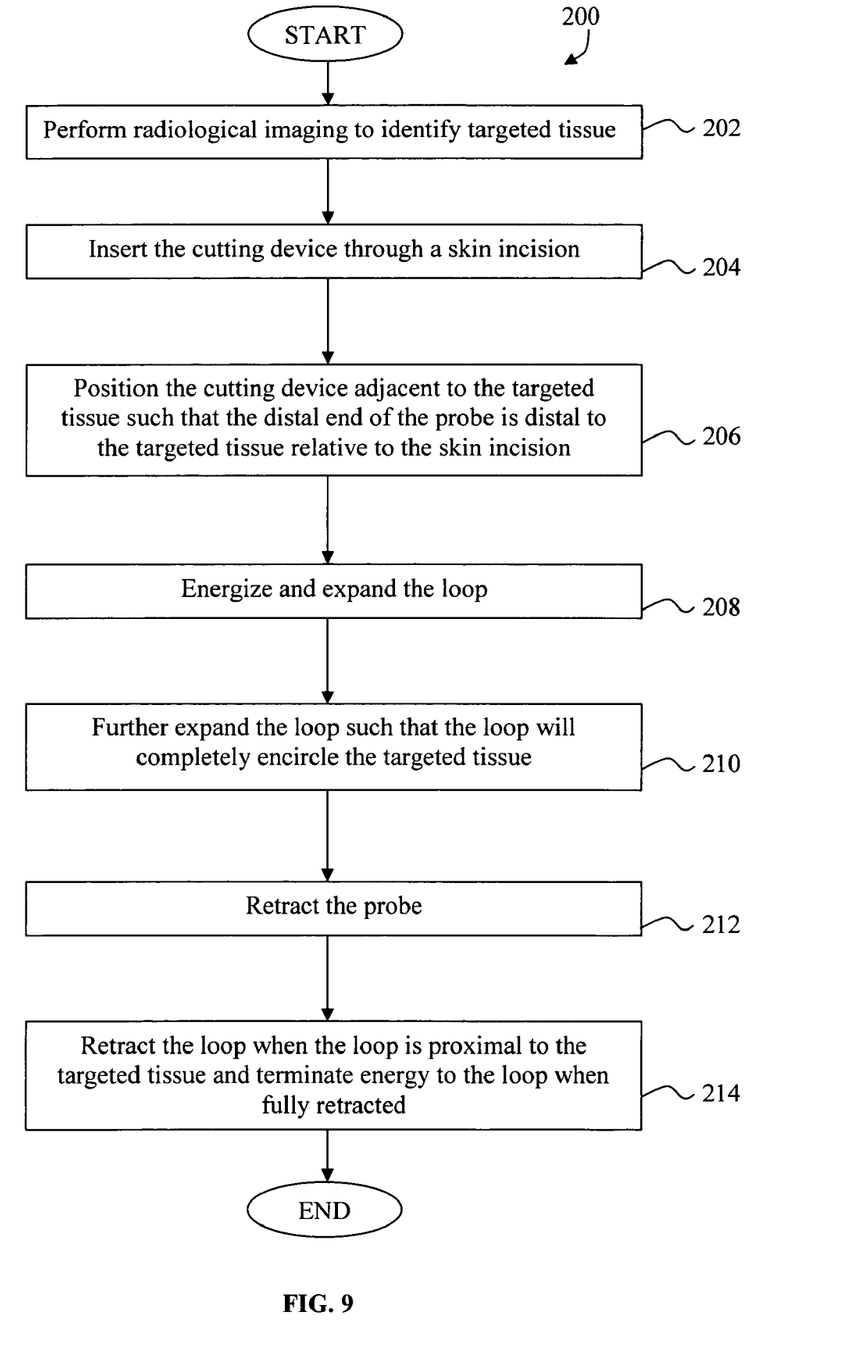
FIG. 9 is a flowchart illustrating an imaging and cutting process employing the bendable cutting device.

FIG. 9 is a flowchart illustrating a cutting process 200 employing the cutting device and using an imaging device to guide the procedure. At step 202, radiological imaging, preferably axial ductal ultrasound scanning, is performed on the breast to identify a targeted volume of soft tissue that includes a lesion and the duct and/or lobe in which the lesion has developed. Preferably the targeted tissue also includes any extension of the lesion or disease process (e.g., extension of disease within the duct, growth into Cooper's ligament and multifocal lesions). The axial ductal ultrasound scanning is preferably performed prior to the cutting process 200 to delineate the lesion size, shape and position relative to the duct(s) and the lobe, and to identify disease extension within the duct(s), growth into Cooper's ligament and multifocal lesions. The axial ductal ultrasound scanning may be enhanced with the use of ultrasound contrast agents, such as described in co-pending U.S. patent application Ser. No. 10/167,017, entitled "Ultrasound Imaging Of Breast Tissue Using Ultrasound Contrast Agent" and filed on Jun. 11, 2002, the entirety of which is incorporated by reference herein. The axial ductal ultrasound images may be processed to give images that are at least one of two-dimensional, three-dimensional and four-dimensional images.

At step 204, the cutting device is inserted through a skin incision on the breast. The incision is typically made in relatively close proximity to the targeted tissue being imaged. Preferably, the incision is made at the areolar border to provide for improved cosmesis. Prior to making the skin incision, the imaging and cutting process may be facilitated with the use of a soft tissue orientation and imaging guide system, such as that describe in co-pending U.S. patent application Ser. No. 10/284,990, entitled "Soft Tissue Orientation and Imaging Guide Systems and Methods" and filed on Oct. 31, 2002, the entirety of which is incorporated by reference herein.

At step 206, the cutting device, preferably guided using the medical imaging, is positioned adjacent to the targeted tissue in preparation for the cutting process. Preferably, the targeted tissue includes the entire lesion and the diseased duct(s) containing any extension of the lesion, multifocal lesions, growth into Cooper's ligament or the entire lobe or part of the lobe containing the lesion. During the positioning of the cutting device, the loop is held in the penetrating configuration to facilitate penetration into the soft tissue. The loop may be energized from an external energy source such as a radio frequency generator. The distal end of the probe is positioned distal to the targeted tissue relative to the skin incision.

At step 208, the loop is energized and expanded which moves the loop from the penetrating configuration to the cutting configuration. As the loop moves to the cutting configuration, tissue is cut along the path of movement.

At step 210, the loop is further expanded to increase the size of the loop such that the loop can create a circumferential cut around the targeted tissue. The height and/or width of the loop is preferably adjusted before and/or during the cutting process. Preferably the circumferential cut includes a satisfactory margin of normal tissue surrounding the lesion, the diseased ducts(s), growth into Cooper's ligament and/or multifocal lesions.

At step 212, the probe is retracted which causes the loop to create a circumferential cut around the targeted tissue. During the cutting process, the loop and/or probe may oscillate or move in a back and forth in an independent motion that is separate from the advancement or retraction of the probe to facilitate the cutting process. Preferably the imaging device images the loop and/or area of tissue adjacent to the loop during the cutting process.

At step 214, when the loop is proximal to the targeted tissue relative to the skin incision, the loop is retracted and energizing of the loop terminated, completing the cutting process 200. During the cutting process or after the cutting process is complete, a tissue collector may be employed to encompass the targeted tissue that has been cut to facilitate removal from the breast. A tissue marking system may also be employed to facilitate orientation of the targeted tissue once removed from the breast.

In an alternative, during step 206, the distal end of the probe is positioned proximal to the targeted tissue relative to the skin incision. At step 212, the probe is advanced causing the loop to create a circumferential cut around the targeted tissue. At step 214, when the loop is distal to the targeted tissue the loop is retracted.

While the exemplary embodiments of the present invention are described and illustrated herein, it will be appreciated that they are merely illustrative and that modifications can be made to these embodiments without departing from the spirit and scope of the invention. Thus, the scope of the invention is intended to be defined only in terms of the following claims as may be amended, with each claim being expressly incorporated into this Description of Specific Embodiments as an embodiment of the invention.

What is claimed is:

1. A tissue cutting device, comprising:
   a probe having a length generally defining a probe axis, the probe defining at least one cutting loop exit at an exit angle relative to the probe axis, the exit being at a distal region of the probe;
   a cutting loop with shape memory having a preconfigured shape, the cutting loop being selectively in one of a penetrating configuration configured for the cutting device to penetrate tissue and a cutting configuration configured for the cutting loop to cut tissue, the cutting loop being generally parallel to the probe axis and generally within a profile of the probe and generally disposed outside of the probe in the penetrating configuration, and when in the cutting configuration, the cutting loop extends through the cutting loop exit and generally returns to the preconfigured shape and generally defines a cutting configuration plane, the cutting loop being at a cutting angle relative to the probe axis generally defined by the exit angle and the probe axis being non-parallel to the cutting configuration plane; and
   a cutting loop securing mechanism configured to selectively secure the cutting loop in the penetrating configuration and to release the cutting loop into the cutting configuration, the cutting loop securing mechanism being one of slidably disposed relative to the probe and a groove defined in the probe proximal to the cutting loop exit.

2. The device of claim 1, wherein the cutting loop securing mechanism extends from a distal end of the probe and is at least partially slidably retractable into the probe.

3. The device of claim 2, wherein the cutting loop securing mechanism is Y-shaped.

4. The device of claim 1, wherein the cutting loop securing mechanism is a cover slidably disposed over probe and configured to secure the cutting loop between the loop cover and the probe for the penetrating configuration.

5. The device of claim 1, wherein the cutting loop securing mechanism is the groove defined in the probe proximal to the cutting loop exit.

6. The device of claim 1, wherein the probe includes at least one cutting loop channel terminating at the cutting loop exit.

7. The device of claim 1, wherein the size of the cutting loop is adjustable by retracting or extending the cutting loop into and out of the probe when the cutting loop is in a cutting configuration.

8. The device of claim 1, wherein the probe defines two cutting loop exits through which the cutting loop extends.

9. The device of claim 1, wherein the cutting loop exit is selectively positionable about the probe to facilitate adjusting a width of the cutting loop.

10. The device of claim 1, wherein the cutting loop exit is selectively positionable to adjust the exit angle between the cutting loop exit and the probe.

11. The device of claim 1, wherein at least one edge of the cutting loop is at least one of sharpened and serrated.

12. The device of claim 1, further comprising a tissue penetrator at a distal end of the probe, the tissue penetrator being coupled to an energy source for supplying energy to the tissue penetrator to facilitate tissue penetration.

13. The device of claim 12, wherein the tissue penetrator is partially insulated to selectively expose the tissue to the energy.

14. The device of claim 1, wherein the probe defines an opening at a distal end of the probe through which the cutting loop may selectively extend for the cutting configuration and retract for the penetrating configuration.

15. The device of claim 1, further comprising a loop cover disposed slidably over probe, the loop cover configured to secure the cutting loop between the loop cover and the probe for the penetrating configuration and to release the cutting loop into its preconfigured shape for the cutting configuration.

16. The device of claim 1, wherein the cutting loop is coupled to an energy source configured to supply energy to the cutting loop to facilitate cutting of tissue by the cutting loop.

17. The device of claim 16, wherein the energy source is selected from at least one of a radio frequency, laser, water jet, air abrasion, ultrasonic, oscillation along a predetermined distance, direction and/or frequency, oscillation along a variable distance, direction and/or frequency.

18. The device of claim 16, wherein the cutting loop is partially insulated to selectively expose the tissue to the energy.

19. The device of claim 1, further comprising an imaging device generally housed in the probe.

20. The device of claim 1, further comprising a probe locating mechanism housed in the probe, the probe locating mechanism facilitates in determining the location of at least one of the probe and the cutting loop within the tissue from external to the tissue, the probe locating mechanism being one of a light, a radiologic marker, and an ultrasound marker.

21. The device of claim 1, further comprising a tissue collector to collect tissue cut by the cutting loop.

22. A method for cutting targeted tissue, comprising:
    positioning a tissue cutting device adjacent to the targeted tissue, such that a distal end of a probe of the tissue cutting device is distal to the targeted tissue, the probe having a length generally defining a probe axis and the probe defining at least one cutting loop exit at an exit angle relative to the probe axis, the exit being at a distal region of the probe;
    releasing a cutting loop of the tissue cutting device from being generally parallel to the probe axis and generally disposed outside of the probe in a penetrating configuration to a cutting configuration, the cutting loop being in and in contact with soft tissue during the releasing, the cutting loop having shape memory with a preconfigured shape such that upon releasing the cutting loop, the cutting loop generally returns to the preconfigured shape and generally extends at a cutting angle relative to the probe axis defined by the exit angle; and
    retracting the tissue cutting device so that the cutting loop in the cutting configuration cuts the targeted tissue.

23. The tissue cutting method of claim 22, further comprising returning the cutting loop to the penetrating configuration when the cutting loop is proximal to the targeted tissue.

24. The tissue cutting method of claim 22, further comprising applying an energy to the cutting loop to facilitate cutting of tissue during the retracting.

25. The tissue cutting method of claim 24, wherein the energy is selected from the group consisting of radio frequency energy, laser, water jet, air abrasion, ultrasonic, and oscillation.

26. The tissue cutting method of claim 24, wherein the cutting loop is partially insulated to selectively expose the tissue to the energy being applied.

27. The tissue cutting method of claim 22, wherein the positioning includes applying an energy to a tissue penetrator at a distal end of the probe to facilitate tissue penetration.

28. The tissue cutting method of claim 27, wherein the tissue penetrator is partially insulated to selectively expose the tissue to the energy being applied.

29. The tissue cutting method of claim 22, further comprising scanning the tissue with an imaging device and determining the targeted tissue to be cut.

30. The tissue cutting method of claim 29, wherein the imaging device is housed by the probe.

31. The tissue cutting method of claim 22, further comprising adjusting the size of the cutting loop to generally encircle the targeted tissue.

32. The tissue cutting method of claim 22, wherein the retracting is such that a tissue collector follows the path of the cutting loop to collect the cut tissue.

* * * * *